United States Patent [19]

Hochman

[11] Patent Number: 5,902,732
[45] Date of Patent: May 11, 1999

[54] DRUG SCREENING PROCESS MEASURING CHANGES IN CELL VOLUME

[75] Inventor: Daryl W. Hochman, Seattle, Wash.

[73] Assignee: Cytoscan Sciences LLC, Mercer Island, Wash.

[21] Appl. No.: 08/539,296

[22] Filed: Oct. 4, 1995

[51] Int. Cl.[6] .............................. C12Q 1/02; C12M 1/34
[52] U.S. Cl. .......................................... 435/29; 435/288.7
[58] Field of Search .................................... 435/29, 288.7

[56] References Cited

U.S. PATENT DOCUMENTS

| | | | |
|---|---|---|---|
| 4,284,355 | 8/1981 | Hansen et al. | 356/335 |
| 5,162,204 | 11/1992 | Matsuzaki et al. | 435/29 |
| 5,215,095 | 6/1993 | Macvicar et al. | 128/665 |
| 5,270,173 | 12/1993 | Yonemori et al. | 435/29 |
| 5,580,748 | 12/1996 | Alkon et al. | 435/29 |
| 5,605,811 | 2/1997 | Seubert et al. | 435/29 |

OTHER PUBLICATIONS

Guggino et al. CA:103:102292j; J. Gen. Physiol, 86(1):31–58, 1985.
Meda et al., Nature 374:647–650, 1995. Month Not Available.
Mark et al., Neurobiology Aging 16:187–198,1995. Month Not Available.
Harris et al., Exp. Neurol. 131:193–202,1995. Month Not Available.
Behl et al., Biochem. Biophys. Res. Comm. 197:9490956, 1993. Month Not Available.
Yamamoto et al., J. Neurobio. 25:585–594, 1994. Month Not Available.
Goodman et al., Brian. Res. 645:171–176, 1994. Month Not Available.
Kumar et al., Intern. J. Neurosci. 79:185–190, 1994. Month Not Available.
Pike and Cotman, Neuroscience 56:269–274, 1993. Month Not Available.
Behl et al., Cell 77:817–827, 1994. Month Not Available.
Hensley et al., Proc. Natl. Acad. Sci. USA 91:3270–3274, 1994. Month Not Available.

*Primary Examiner*—Gary L. Kunz
*Attorney, Agent, or Firm*—Jeffrey B. Oster

[57] ABSTRACT

There is disclosed a method for screening drug candidate compounds for anti-epileptic activity, a method for screening drug candidate compounds for activity to prevent or treat symptoms of Alzheimer's disease, and a method for determining cell viability and health of living cells inside polymeric tissue implants.

14 Claims, 6 Drawing Sheets

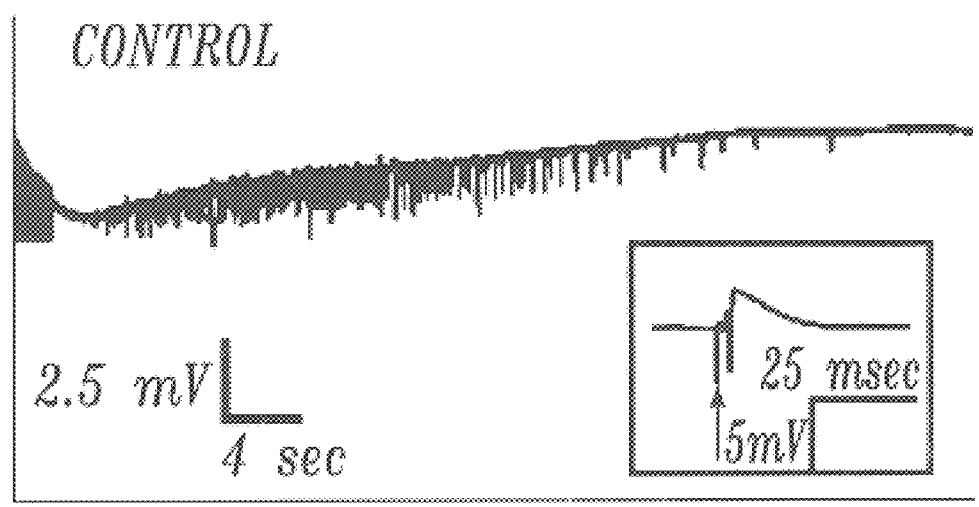
Fig. 1A
Fig. 1A1

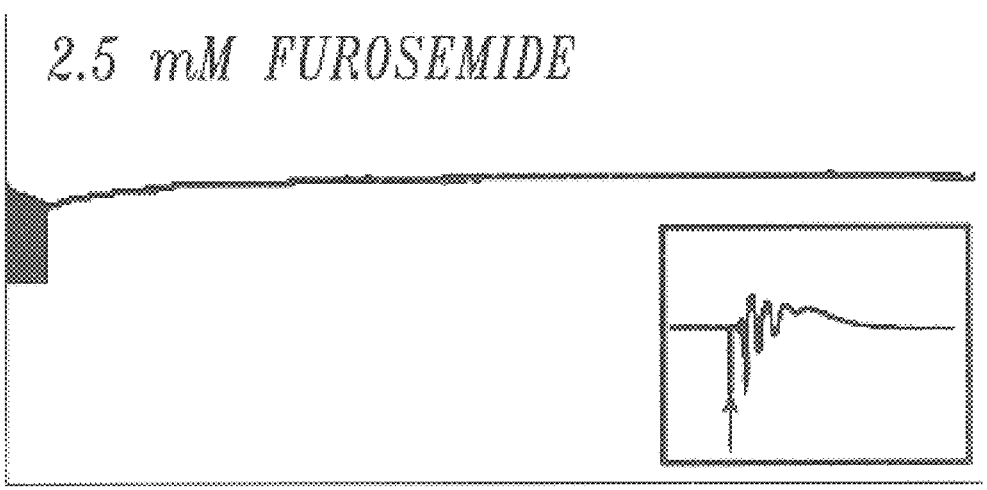
Fig. 1B
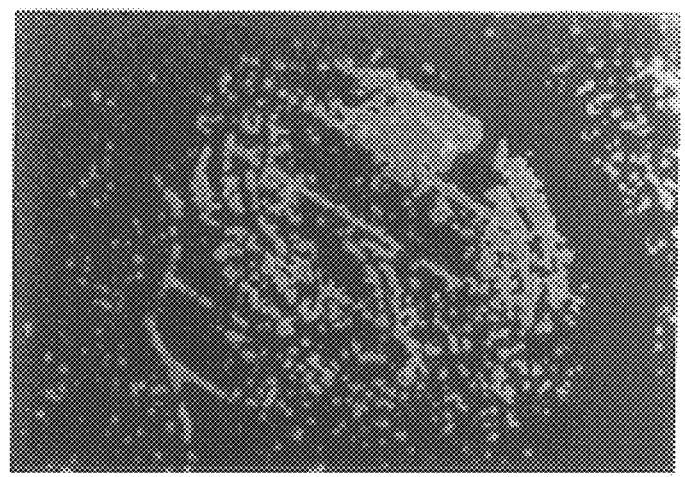
Fig. 1B1

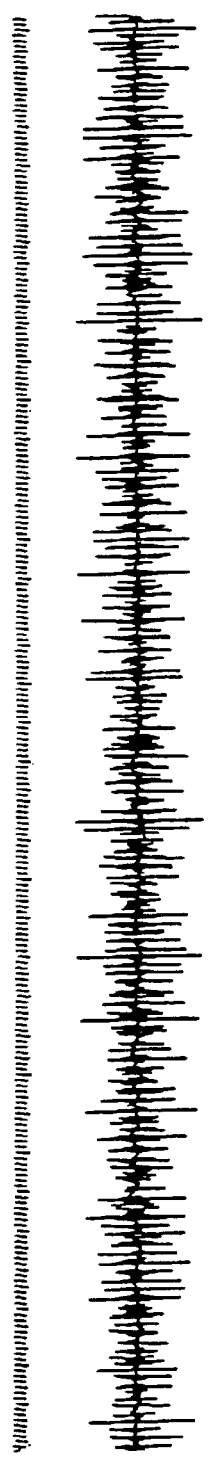
Fig. 3A
Fig. 3B
Fig. 3C
Fig. 3D
Fig. 3E
Fig. 3F
Fig. 3G
Fig. 3H

DRUG SCREENING PROCESS MEASURING CHANGES IN CELL VOLUME

TECHNICAL FIELD OF THE INVENTION

The present invention provides a method for screening candidate drug compounds for changes in cell swelling in response to a stressing agent as a predictive model for anti-epileptic activity and apoptosis, including Alzheimer's Disease and for attenuating glutamate excitotoxicity to decrease morbidity associated with stroke and neurodegenerative disorders.

BACKGROUND OF THE INVENTION

The maintenance of cell volume is a fundamental property of all eukaryotic cells. The cell membrane of animal cells is highly permeable to water, the cell volume will be determined by the cellular content of the osmotically active solutes and by the osmolality of the extracellular fluid. The intracellular and extracellular environments are significantly different. A combination of active and passive transport processes are involved in cell volume regulation. Viable and healthy cells maintain constant cell volumes under resting conditions and are capable of counteracting volume perturbations by performing volume recovery processes.

Swollen cells tend to reduce their volume often by losing KCl and by concomitant loss of cell water. This is known as a "regulatory volume decrease (RVD). Similarly, shrunken cells show the capacity to increase their volume to initial or normal healthy values by taking up extracellular KCl and the concomitant uptake of cell water. This is known as "regulatory volume increase" (RVI).

The process of volume regulation involves a large number of transport systems and signaling mechanisms. Now, the only way to measure the "health" of cells is to wait for cell death and measure live versus dead cells by dye exclusion or the ability to grow into colonies. Similarly, the only way to measure apoptosis has been through a difficult and cumbersome process of cell sorting. The process of cell sorting does not lend itself to high throughput mechanisms. However, there is a need in the art to develop high throughput screening mechanisms to measure cell "health" and not just cell death and to measure the beginnings of the process of apoptosis rapidly and inexpensively. The present invention, using an epilepsy screening model, developed a novel and inexpensive high throughput screening system for cellular health and apoptosis that is applicable to evaluate compounds for a variety of treatment indications wherein the underlying diseases and their pathology (on a cellular level) is caused by poor cell health of certain cell types and apoptosis.

Two primary features that characterize epileptiform activity are hyperexcitability and hypersynchronization (Schwartzkroin, in *The Treatment of Epilepsy: Principles and Practice*, E. Wylie, Ed. Lea & Febiger, Philadelphia, 1993, pp. 83–98.). Although either of these features alone might be sufficient for the development and spread of epileptiform activity, it has not been possible to dissociate them in experimental models of epilepsy. Some studies have suggested that nonsynaptic mechanisms might be sufficient to produce hyperexcitability and/or hypersynchrony. For example, exposing hippocampal slices to calcium-free medium abolished synaptic transmission but produced synchronized burst discharges in a CA1 subfield (Jefferys and Haas, *Nature* 200:448, 1982; Taylor and Dudek, *Science* 218:810, 1982; Konnerth et al., *Exp. Brain Res.* 51:153, 1984; and Richardson et al., *Brain Res.* 294:255, 1984). Synchronized activity may be mediated by ephaptic interactions among the densely packed CA1 neurons (Dudek et al., *Basic Mechanisms of the Epilepsy's: Molecular and Cellular Approaches*, Delgado-Escueta et al. Eds. Raven Press, New York 44:593–617, 1986).

A major component of volume regulation of the ECS (extracellular space) under normal and pathological conditions is glial dependent (Kimelberg and Ransom, in *Astrocytes: Cell Biology and Pathology of Astrocytes*, Fedoeroff and Vernadakis, Eds. Academic, New York, 3:129–166, 1986). A furosemide-sensitive Na-K-2Cl cotransporter plays a major role in cell swelling and volume-regulation of astrocytes in cell culture (Geck et al., *Biochim. Biophys. Acta* 600:432, 1980; Walz et al., *J Cerebr. Blood Flow Metab.* 4:301, 1984; and Kimelberg and Frangakis, *Brain Res.* 361:125, 1985). Changes in external K+ concentrations alter intracellular KCl concentrations in astrocytes. The changes are thought to act through furosemide-sensitive Na-K-2Cl cotransport, accompanied by osmotically-driven water movement. Furosemide blocks glial cell swelling (Kimelberg and Ransom, in *Astrocytes: Cell Biology and Pathology of Astrocytes*, Fedoeroff and Vernadakis, Eds. Academic, New York, 3:129–166, 1986; Geck et al., *Biochim. Biophys. Acta* 600:432, 1980; Walz and Hertz, *J Cerebr. Blood Flow Metab.* 4:301, 1984; and Kimelberg and Frangakis, *Brain Res.* 361:125, 1985). However, the concentrations that furosemide acts are well beyond those than can be achieved in a clinical setting. Therefore, there is a need in the art to device a system, including hardware and software, that is able to screen for active drug compounds in culture in a high-throughput screening assay system. The present invention utilized furosemide to develop such a screening system.

Glutamate plays a vital role in the normal functioning of neurons. It is the main excitatory neurotransmitter in the central nervous system (CNS). The normal function of glutamate, as a means of communication from one neuron to the next, breaks down in certain disease states. Damage to the CNS associated with ischemia, most commonly in cerebrovascular embolitic disease or stroke, is a direct result of hypoxia or deprivation of metabolic intermediates. Glutamate is excessively effluxed during hypoxia by ischemic neurons, which in turn, activates pathways in post-synaptic neurons leading to acute cell swelling and later, cell death. Astrocytes maintain ionic, amino acid neurotransmitter and water homeostasis in the extracellular space of the brain. When applied to a culture of astrocytes, glutamate (at concentrations from 50 $\mu$M to 1 mM) caused cell swelling (Juurlink et al., *Can. J Physiol. Pharm.* 70:5344–9, 1992). There is a need in the art to discover drug products administered as early as possible after the ischemic event, that can attenuate the damaging action of glutamate and decrease morbidity associated with stroke and other neurodegenerative disorders.

Necrosis and apoptosis are two distinct modes of cell death which differ in morphology, mechanism and incidence. Apoptosis plays an important role in embryogenesis and development and in tumor growth. Apoptosis is characterized by cell shrinkage, chromatin condensation and systematic DNA cleavage. Apoptotic cells are rapidly engulfed by phagocytic cells to prevent an inflammatory reaction to degredative cell contents. Apoptosis has not been identified in vivo due to problems of heterogeneity and short half life of an apoptotic cell. Apoptosis has been characterized in vitro using dyes and flow cytometry (Dive et al., *Biochem. Biophys. Acta* 1133:275–85, 1992). However, flow cytometry is an extremely time consuming and laborintensive process that cannot be used for high-throughput screening procedures that needs to investigate large numbers of candidate drug products. Therefore, there is a need in the art to find drug candidates from large libraries of compounds that appear to have therapeutic activity to reverse or prevent the apoptotic process and thus exhibit potential therapeutic utility in treating or preventing the progression of degenerative diseases such as Alzheimer's Disease (AD) and other neurodegenerative diseases.

AD is characterized by the accumulation of amyloid plaques, neurofibrillary degeneration, and accompanying neuronal loss. AD amyloid assembles into compact fibrous deposits from the beta amyloid protein (BAP), which is a proteolytic fragment of the membrane-associated amyloid precursor protein of 39–43 amino acids in length. The neurotoxicity of BAP has been observed in vitro in cell culture and it appears to induce an apoptotic death. Similarly, glutamate will cause cell death of neuronal cells in culture and first cause cell swelling.

There are new technologies being developed that involve creating functioning cells that secrets biologically active materials. Such cellular cultures are encapsulated in polymeric materials that avoid problems of antigen recognition and rejection. However, in manufacturing such "living" therapeutic devices, it is important to check on the quality of such devices by measuring the health and viability of the cells encapsulated during various stages of the manufacturing process and prior to use. Therefore, there is a need in the art to develop processes and devices for measuring the health and viability of encapsulated cells of living cellular implants.

SUMMARY OF THE INVENTION

The present invention provides a method for screening drug candidate compounds for anti-epileptic activity comprising:

(a) providing a culture of viable glial cells and dividing the culture into components that will become control samples and test samples;

(b) adding a glial cell stressing agent at a concentration that is capable of osmotically shocking the glial cells but not killing the glial cells;

(c) adding the drug candidate at varying concentrations to only test samples of glial cells; and (d) measuring whether the drug candidate in the test samples is capable of abating changes in glial cell swelling in the control samples when measured by a means for measuring cellular dimensions over time. Anti-epileptic activity refers to therapeutic agents which block or prevent hypersynchronization characteristic of a seizure.

Preferably, the measuring means for glial cell swelling measures intrinsic optical signals. Preferably the glial cell stressing agent is a hypotonic medium having a lowered $Mg^{++}$ concentration. Preferably the means for measuring intrinsic optical signals is by comparing digitized video images of the cell culture magnified and then subtracting the digitized images after addition of the stressing agent to form a changes images that can integrate cellular swelling changes measure over time.

The present invention further provides a method for screening drug candidate compounds for activity to prevent or treat symptoms of Alzheimer's disease comprising:

(a) providing a culture of viable CNS-based cells and dividing the culture into components that will become control samples and test samples;

(b) adding a sensitization agent at a concentration that is capable of inducing apoptosis in the CNS-based cells but not killing the cells and further adding an osmotic stressing agent;

(c) adding the drug candidate at varying concentrations to only test samples of cells; and (d) measuring whether the drug candidate in the test samples is capable of abating changes in cell swelling in the control samples when measured by a means for measuring cellular dimensions over time. The CNS-based cells are selected from the group consisting of glial cells, neuronal cells, microglia, astrocytes, and combination cultures thereof. The sensitization agent is selected from the group consisting of BAP and derivatives thereof, glutamate, IFN-γ (interferon gamma), TNFα (tumor necrosis factor alpha), and combinations thereof.

Preferably, the measuring means for CNS-based cell swelling measures intrinsic optical signals. Preferably, the osmotic stressing agent is a hypotonic medium having lowered $Mg^{++}$ concentrations. Preferably the means for measuring intrinsic optical signals is by comparing digitized video images of the cell culture magnified and then subtracting the digitized images after addition of the stressing agent to form a changes images that can integrate cellular swelling changes measure over time.

The present invention further provides a method for screening drug candidate compounds for activity to prevent or CNS damage resulting from ischemia comprising:

(a) providing a culture of viable CNS-based cells and dividing the culture into components that will become control samples and test samples;

(b) adding a sensitization agent at a concentration that is capable of inducing apoptosis in the CNS-based cells but not killing the cells and further adding an osmotic stressing agent;

(c) adding the drug candidate at varying concentrations to only test samples of cells; and (d) measuring whether the drug candidate in the test samples is capable of abating changes in cell swelling in the control samples when measured by a means for measuring cellular dimensions over time. The CNS-based cells are selected from the group consisting of glial cells, neuronal cells, microglia, astrocytes, and combination cultures thereof The sensitization agent is selected from the group consisting of BAP and derivatives thereof, glutamate, IFN-γ (interferon gamma), TNFα (tumor necrosis factor alpha), and combinations thereof.

Preferably, the measuring means for CNS-based cell swelling measures intrinsic optical signals. Preferably, the osmotic stressing agent is a hypotonic medium having lowered $Mg^{++}$ concentrations. Preferably the means for measuring intrinsic optical signals is by comparing digitized video images of the cell culture magnified and then subtracting the digitized images after addition of the stressing agent to form a changes images that can integrate cellular swelling changes measure over time.

The invention further provides a method for determining cell viability and health of living cells inside polymeric tissue implants, comprising:

(a) providing a sample of tissue implants comprising living cells inside a polymeric matrix;

(b) measuring the cellular dimensions of the living cells inside the tissue implant by determining cellular dimensions with a microscopic means for determining digitized video images over time.

(c) adding a hypo osmotic stressing agent at a concentration that is capable of osmotically shocking the living cells but not killing the living cells; and (d) measuring whether the osmotic stressing agent was capable of inducing changes in living cell swelling which would indicate poor health of the living cells.

Preferably, the measuring means for living cell swelling measures intrinsic optical signals. Preferably the cell stressing agent is a hypotonic medium having a lowered $Mg^{++}$ concentration. Preferably the means for measuring intrinsic optical signals is by comparing digitized video images of the living cells culture magnified and then subtracting the digitized images after addition of the stressing agent to form a changes images that can integrate cellular swelling changes measure over time.

BRIEF DESCRIPTION OF THE DRAWINGS

FIG. 1 shows the effect of furosemide on stimulation evoked after discharge activity. The gray-scale photo shown in FIG. 1D shows a video image of a typical hippocampal slice in the recording chamber. The fine gold-wire mesh that was used to hold the tissue in place can be seen as dark lines running diagonally across the slice. A stimulating electrode can be seen in the upper right resting on the stratum radiatum of CA1. The recording electrode (too thin to be seen in the photo) was inserted at the point indicated by the white arrow. (A) Two FIG. 1A illustrates that two seconds of stimulation at 60 Hz elicited after discharge activity. FIG. 1A shows a typical after discharge episode recorded by the extracellular electrode; inset shows the CA1 field response to a single 200 sec test pulse (artifact at arrow) delivered to the Schaffer collaterals. FIG. 1A shows a map of the peak change in optical transmission through the tissue evoked by Schaffer collateral stimulation. The region of maximum optical change corresponds to the apical and basal dendritic regions of CA1 on either side of the stimulating electrode. FIG. 1B illustrates sample traces showing responses to stimulation after 20 minutes of perfusion with medium containing 2.5 mM furosemide. Both the electrical after discharge activity (shown in FIG. 1B) and the stimulation-evoked optical changes (shown in FIG. 1B) were blocked. However, there was a hyperexcitable field response (multiple population spikes) to the test pulse (inset). FIGS. 1C and 1C1 illustrate that restoration of initial response patterns was seen after 45 minutes of perfusion with normal bathing medium.

FIG. 3 shows furosemide blockade of kainic acid-evoked electrical "status epilepticus" in a urethane-anesthetized rat. EKG (top trace) and cortical EEG (bottom trace) were recorded continuously during 3-4 hour experiments. FIG. 3A shows the baseline EKG and EEG activity before KA injection. FIG. 3B shows a seizure-like EEG pattern, 60 minutes after KA injection (12 mg/kg/i.v.). FIG. 3C shows initial furosemide blockade of seizure-like EEG, 120 minutes after KA and 20 minutes after the second furosemide injection (each injection was 20 mg/kg). FIG. 3C shows that thirty minutes after (C), complete furosemide blockade of the seizure-like EEG. Note that onset of the KA-induced seizure-like EEG (FIG. 3B) is associated with a significant increase in heart-rate; furosemide had no further effect on EKG (cf. FIGS. 3B and 3C), even when the electrical seizure-like discharge was blocked. Control experiments with KA alone showed that KA-induced seizure-like activity persisted for at least 3 hours in the absence of other treatment.

DETAILED DESCRIPTION OF THE INVENTION

Epilepsy

Figure 1C:
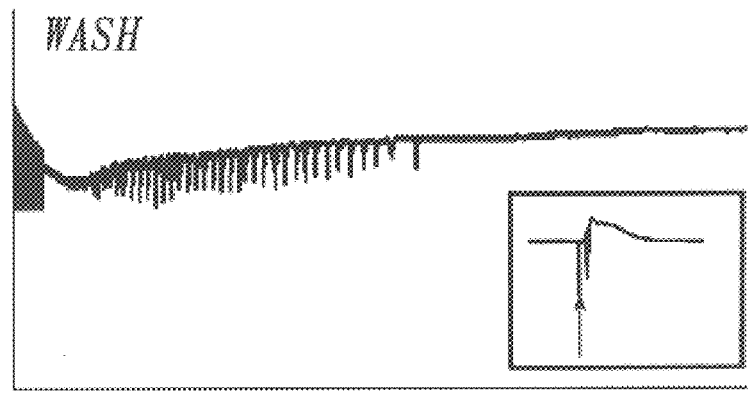

The present invention provides a method for screening drug candidate compounds for anti-epileptic activity comprising:

(a) providing a culture of viable glial cells and dividing the culture into components that will become control samples and test samples;

(b) adding a glial cell stressing agent at a concentration that is capable of osmotically shocking the glial cells but not killing the glial cells;

(c) adding the drug candidate at varying concentrations to only test samples of glial cells; and (d) measuring whether the drug candidate in the test samples is capable of abating changes in glial cell swelling in the control samples when measured by a means for measuring cellular dimensions over time.

Preferably, the measuring means for glial cell swelling measures intrinsic optical signals. Preferably the glial cell stressing agent is a hypotonic medium having a lowered $Mg^{++}$ concentration. Preferably the means for measuring intrinsic optical signals is by comparing digitized video images of the cell culture magnified and then subtracting the digitized images after addition of the stressing agent to form a changes images that can integrate cellular swelling changes measure over time. A preferred device for measuring optical intrinsic signals is described below.

The data provided herein with hippocampal slices provides the basis for the present invention. These data provide conclusive evidence in epilepsy that changes in the extracellular space (ECS) are critical for the generation of epileptiform activity. Moreover, the means for determining this was determination of intrinsic signal through a comparison of digitized video images over time in response to a stressing agent. Glial cell swelling is necessary for hypersynchronization (simultaneous discharge of a population of neurons) that characterizes epilepsy. These data provide evidence that one is able to screen for anti-epileptic drugs using cultures of glial cells. The inventive method provides a method for observing (with digitized video images magnified microscopically) agents that can block glial cell swelling response to an osmotic "stressing" agent. The method involves observing a cell culture containing a sparse population of glial cells. The glial cells are first perfused with artificial cerebral spinal fluid (ACSF).

Changes in ECS volume in tissue slices can be continuously monitored by measuring changes in tissue-light-scattering or reflectance (intrinsic optical signal) (Lipton, *J Physiol.* (Lond.) 231:365, 1973). By monitoring this signal with video-imaging techniques, it has been shown that fuirosemide blocks synaptically evoked changes in light-transmission through the CA1 region of hippocampal slices without inhibiting the synaptic response to Schaffer collateral stimulation (MacVicar and Hochman, *J Neurosci.* 11: 1458, 1991). The furosemide-treated tissue actually showed a hyperexcited synaptic response in the form of multiple population spikes (Id.).

The present invention is based upon the surprising result that the intrinsic optical signal of volume change of the ECS was due to activity-evoked glial swelling. Further, glial cell swelling, as measured by intrinsic optical signal, was blocked by the loop diuretic furosemide. The enhanced synaptic response was consistent with results of other studies (Misgeld et al, Science 232:1413, 1986; Thompson et al., *J. Neurophysiol.* 60:105, 1988; and Thompson and G ähwiler, *J. Neuropysiol.* 61:512, 1989; and Pearce, *Neuron* 10:189, 1993) showing that, in hippocampal and cortical pyramidal cells, furosemide decreases inhibition by causing a depolarizing shift in the equilibrium potential for $Cl^-$. The experimental data reported herein suggest that: (1) mechanisms of neuronal synchronization involved in epileptiform activity can be dissociated from processes underlying changes in synaptic excitability; (2) nonsynaptic mechanisms, associated with furosemide-sensitive changes in cell-volume regulation, are critical for hypersynchronization of neuronal activity; and (3) agents that affect the size of the extracellular space may have clinical utility as anti-epileptic drugs.

The inventive method involves observing a culture comprising a sparse population of glial cells, which are first perfused with ACSF. After equilibration, video images are acquired and stored in memory with reference to each culture imaged. The cultures are perfused with hyper osmotic medium of about 350 mOsm rather than a physiologic 290 mOsm or with ACSF containing a higher potassium of about 10 mM. After several minutes, images are acquired of the now swollen glial cells at the precise location (x-y coordinates on an inverted stage microscope) that the control images were acquired.

The images (control and osmotic shock) are compared by an edge-detection operation using a difference of Gaussians operation along with the standard deviations of the differences in cell diameters between control and stressed (hyper- or hypo-osmotic) conditions. This operation is automated with appropriate control software. Following determination of the characteristic swelling response for each culture, the cells are treated with varying doses of the test drug to test the response of the "treated" cells to the stressing agent with diameter changes again recorded in a similar fashion. If a candidate drug attenuated or blocked swelling of glial cells, it is considered a "hit" and a candidate for further investigation.

Alzheimer's Disease

The present invention further provides a method for screening drug candidate compounds for activity to prevent or treat symptoms of Alzheimer's disease comprising:

(a) providing a culture of viable CNS-based cells and dividing the culture into components that will become control samples and test samples;

(b) adding a sensitization agent at a concentration that is capable of inducing apoptosis in the CNS-based cells but not killing the cells and further adding an osmotic stressing agent;

(c) adding the drug candidate at varying concentrations to only test samples of cells; and (d) measuring whether the drug candidate in the test samples is capable of abating changes in cell swelling in the control samples when measured by a means for measuring cellular dimensions over time. The CNS-based cells are selected from the group consisting of glial cells, neuronal cells, microglia, astrocytes, and combination cultures thereof The sensitization agent is selected from the group consisting of BAP and derivatives thereof, glutamate, IFN-γ (interferon gamma), TNFα (tumor necrosis factor alpha), and combinations thereof.

Preferably, the measuring means for CNS-based cell swelling measures intrinsic optical signals. Preferably, the osmotic stressing agent is a hypotonic medium having lowered $Mg^{++}$ concentrations. Preferably the means for measuring intrinsic optical signals is by comparing digitized video images of the cell culture magnified and then subtracting the digitized images after addition of the stressing agent to form a changes images that can integrate cellular swelling changes measure over time.

The method for high throughput screening for AD first characterizes normal cellular swelling response in the same manner as for epilepsy, preferably in glial cells. Next, beta-amyloid peptide (BA) is added to the cell cultures in sub-lethal concentrations in a dose-response fashion. After an incubation period of from 1–8 hours, the cells are osmotically stressed with an osmotic stressing agent in the manner described above. The optical method described above is then used to determine which cell cultures are have a normal swelling response and a regulatory volume decrease in response to the return to a normal, healthy culture environment. This procedure is repeated in the presence or absence of a candidate drug at appropriate clinical concentrations. If the comparison of cellular swelling responses of cells is affected by the BA stressing agent, than the candidate drug is positive in this high throughput screen as showing anti-AD activity and a candidate for further investigation.

Primary rat hippocampal neuron cultures are established from embryonic (E-18) Sprague-Dawley rats. The hippocampi are dissected, minced in calcium-free and magnesium-free balanced salt solution and digested with 0.25% trypsin for about 2 minutes. Digestion is stopped with 20% fetal bovine serum and the preparation is centrifuged for about 2 minutes. The cells are resuspended in Dulbecco's Minimal Essential Medium (DMEM), filtered through a 75 micrometer nylon mesh, and plated at a low density in 24 well tissue culture plates precoated with 0.5 mls of a solution of 25 μg/ml polysysine. After 20 min, the media and any unattached cells are removed and the media is replaced with DMEM with 10% fetal bovine serum, 30 mM glucose and 1% penicillin and streptomycin. Four days later, cytosine arabinoside is added to each culture at a concentration of 10 μM to reduce proliferation of non-neuronal cells. After one week the media is removed and replaced with a serum-free media containing 3% bovine serum albumin (BSA). Cultures that are not negative controls receive media containing beta-amyloid protein sufficient to provide a final concentration of 100 µg/ml. Reference marks are added to each well, about equidistant from the walls of the well, prior to coating the wells with poly-lysine. The cultures are examined with the imaging device described herein, preferably viewed through a phase contrast microscope. Additional images are viewed immediately after osmotic stress is applied to the cells, after beta-amyloid is applied, and 12 hr., 24 hr. or 48 hr. later.

Living Tissue Implants

The invention further provides a method for determining cell viability and health of living cells inside polymeric tissue implants, comprising:

(a) providing a sample of tissue implants comprising living cells inside a polymeric matrix;

(b) measuring the cellular dimensions of the living cells inside the tissue implant by determining cellular dimensions with a microscopic means for determining digitized video images over time.

(c) adding a hypo osmotic stressing agent at a concentration that is capable of osmotically shocking the living cells but not killing the living cells; and (d) measuring whether the osmotic stressing agent was capable of inducing changes in living cell swelling which would indicate poor health of the living cells.

Preferably, the measuring means for living cell swelling measures intrinsic optical signals. Preferably the cell stressing agent is a hypotonic medium having a lowered $Mg^{++}$ concentration. Preferably the means for measuring intrinsic optical signals is by comparing digitized video images of the living cells culture magnified and then subtracting the digitized images after addition of the stressing agent to form a changes images that can integrate cellular swelling changes measure over time.

Optical Imaging Screening Apparatus

The inventive methods employ a similar apparatus, comprising a series of components, including video input hardware and dedicated image processing hardware. The video input hardware is, for example, a photo-detector, such as a CCD (charge coupled device) camera (preferably a COHU 6510 CCD Monochrome Camera with a COHU 6500 electronic control box made by COHU Electronics San Diego, Calif.). In some cameras the analog signal is digitized 8-bits deep on an ADI board (analog-to-digital board). The dedicated image processing hardware is generally controlled by a "host computer". The host computer is any common general computer (such as an IBM PC type with an Intel 486, Pentium, or better microprocessor or Sun SPARC) that is interfaced with the dedicated imaging hardware and sends commands to the imaging hardware that direct data flow, computations, image acquisition and the like. Thus, the host computer directs the actions of the imaging hardware and provides the user interface.

The following are definitions of commonly used terms and that are applied in this application according to their art-accepted usage, such as described in Inoue, *Video Microscopy* Plenum Press, New York, 1989.

Area of Interest is that area of tissue that comprises the subject of the image.

Arithmetic Logic Unit (ALU) is the hardware component that performs a variety of mathematical and logic operations (e.g., sum, difference, exclusive or, multiply by a constant, etc.) on the image signal at extremely high speeds.

Averaged Control Image is that updateable image that is the average of a series of real time images over a period of time.

Charge Coupled Device (CCD) is a photo-sensitive silicon chip used in place of a pickup tube in miniature video cameras.

Difference Image is the manipulated image created by adding or subtracting a subsequent image or a particular image in time from an averaged control image.

Frame is a single digitized array of single video pictures.

Frame Buffer is a piece of hardware that serves as a temporary storage of a frame, such as an averaged control image, a subsequent image or a difference image.

Geometric Transformation (Gonzalez and Wintz, *Digital Image Processing*, Addison-Wesley Publishing Co., Reading, 1987) generally modify spatial relationships between pixels in an image. For this reason, geometric transformations are often called "rubber sheet transformations" because they can be viewed as the process of "printing" an image on a sheet of rubber and stretching this sheet according to a predefined set of rules. As applied to video imaging, subsequent images can be viewed as having been distorted due to movement and it is desirable to "warp" these images so that they are similar to the control images. Geometric transformations are distinguished from "point transformations" in that point transformations modify a pixel's value in an image based solely upon that pixel's value and/or location and no other pixel values are involved in the transformation.

Image is a frame or composition of frames that have been altered after digitization, such as processing a sequence of frames into an averaged control image or a subsequent averaged image.

Intrinsic Signal means a detectable change in reflectance properties of neuronal tissue due to endogenous physiologic activity. Possible causes of intrinsic signals include, for example, membrane depolarization, glial cell swelling, cell swelling, ion flux across membranes, blood volume changes, blood deoxygenation (hemoglobin to deoxyhemoglobin), tissue oxygenation and combinations thereof.

Linear Histogram Stretch is a transformation in which the values between two points (high, low) are remapped to cover a full range of values (i.e., dynamic range). For example, the low value is mapped to zero, the high to 255, and the intermediate values are mapped to linearly increasing brightness values. All brightness values below the low value are set to zero and all brightness values above the high value are set to the high value.

Look Up Table (LUT) is a piece of hardware that functions to store memory that directs conversion of the gray value of each pixel into another gray value or color that is specified by the LUT. The LUT can be programmed to manipulate image contrast, threshold an image, apply pseudocolor and the like (such as a convenient implementation method for point processing algorithms). In the case of the present invention, the LUTs are, preferably, implemented for speed on an ADI and/or ALU boards.

Paradigms cause a change in electrical activity of an area of cortical tissue dedicated to a specific function (e.g., speech, language, vision, etc.) thus causing an increase or decrease in what is called an intrinsic signal.

Pixel is the individual units of image in each frame of the digitized signal. The intensity of each pixel is linearly proportional to the intensity of illumination before signal manipulation and corresponds to the amount of emr (photons) being reflected from a particular area of tissue corresponding to a particular pixel. It should be noted that an image pixel is the smallest unit of a digital image and its output intensity can be any value. A CCD pixel is the smallest detecting element on a CCD chip and its analog output is linearly proportional to the number of photons it has detected.

Processed Difference Image is the raw difference image that has been processed or manipulated to filter out noise or movement and increase the dynamics of effect of different pixel values to illustrate events in the area of interest.

The apparatus is made as one unit or a group of components. The first component is a high intensity emr source. The emr source is for illuminating the surface or area of interest, such as a well in a cell culture plate. Different intrinsic signals can be illuminated by different wavelengths of emr. An IR emr source is, for example, a Tunable IR Diode Laser from Laser Photonics, Orlando, Fla. Preferably, the emr source is a high intensity, broad spectrum emr source, such as a tungsten-halogen lamp and a cutoff filter for all wavelengths below 695 nm. Most preferably, the emr source is directed to the area of interest by a fiber optic means. An example of such a emr source is a fiber optic emr passing through a beam splitter, controlled by a D.C. regulated power supply (Lambda, Inc.) and passed through a 695 nm longpass filter.

The inventive apparatus includes a means for obtaining an analog video signal of the area of interest. A preferred device for obtaining an analog video signal is a charge coupled device (CCD) video camera which creates an output video signal at 30 Hz having, for example, 512 horizontal lines per frame using standard RS 170 convention. One such device is a CCD-72 Solid State Camera (Dage-MTI Inc., Michigan) and another such device is a COHU 6500 (COHU, San Diego, Calif.).

The area of interest must be evenly illuminated to better adjust the signal over a full dynamic range. If there is uneven illumination in the area of interest, it will limit the dynamic range. Preferably a high intensity and diffuse or even lighting system is used. Techniques to obtain even illumination over the area of interest include, for example, diffuse lighting, image processing algorithms to compensate for uneven illumination on a digitized image, a constant shade gray image marker point in the area of interest as a control point, a wavelength cutoff filter in front of the camera and/or emr source, or combinations thereof. Preferably, a regulated power supply will prevent fluctuations in emr sources.

The analog signal must first be adjusted to maximize sensitivity of detection (at the level of the analog signal and before digitizing) to amplify the signal and spread the signal across the full possible dynamic range, thereby increasing sensitivity of the apparatus. 60 Hz noise (such as from A.C. power lines) is filtered out in the camera control box by an analog filter. Such adjustments further serve to enhance, amplify and condition the analog signal from the CCD. One means for properly adjusting the input analog signal is to digitize this signal at video speed (30 Hz), and view the area of interest as a digitized image that is converted back to analog.

If the two images (averaged control image and subsequent image) are misaligned prior to subtraction, artifacts will result since the difference image will be more like a gradient image amplifying noise and edge information. Image misalignment can arise from motion. One solution is to fix the camera to a rigid assembly connected to a microscope. Another solution is to perform real time motion compensation with motion detection and geometric transformation with the image processing board. Simple translation or more complicated (thus more accurate) unwarping can be implemented depending upon the input frame rate and amount of averaging.

For many types of images, it is possible to compensate by a geometrical compensation which transforms the image by translation in the x-y plane. In order for an algorithm such as this to be feasible, it must be computationally efficient (preferably implementable in integer arithmetic), memory efficient, and robust with respect to changes in ambient light.

One possible method would be to translate an image by 0 through k number of pixels in every possible direction with respect to the control image. For each of the $(2*k+1)*(2k+1)$ translations, make a subtraction image and calculate some metric to estimate the closeness to the control image. An example of such a metric would be the variance of the subtraction image. The drawback of this method is that it is not efficient since for each of $(2*k+1)*(2k+1)$ subtraction images, one needs to calculate the variance over $512*512$ pixels.

An efficient improvement of this algorithm is to estimate the variance of the subtraction images by randomly selecting some small number of areas of interest (for example, 9 areas of interest), each area consisting of a small number of pixels (say 8×8) from the image that one wishes to translate with respect to the control image. Also, choose some search depth (for example, 10 pixels) over which to translate these small areas of interest with respect to their corresponding areas of interest in the control image. After translation in all possible directions for 0 through 10 pixels, choose the translation which minimizes the variance over the selected areas of interest. Since all the areas of interest are the same size, division is not necessary in the calculation of the variance which is to be ordered so that the minimal variance can be selected. Hence, all calculations can be carried out in integer arithmetic. Since the areas of interest are sufficiently small, most of the data can be read into the host computer's RAM limiting IO to the frame buffers and increasing speed.

Another problem is guaranteeing uniformity in the illumination of the well surface. Nonuniformity comes from fluctuation in the illumination source. Fluctuation in the illumination source is addressed by using a light feedback mechanism to regulate the power supply of the illumination source. Both of these problems can also be compensated for in the image processing module.

The analog video signal is continuously fed into a means for processing the signal. One such means for acquiring and analyzing data is an image analyzer (e.g., Series 151 Image Processor, Imaging Technologies, Inc. Woburn Mass.). An image analyzer can receive and digitize an analog video signal with an analog to digital interface and perform such a function at a frame speed of about 1/30th of a second (e.g., 30 Hz or "video speed"). Processing the signal involves first digitizing the signal into a series of pixels or small squares assigned a value (in a binary system) dependent upon the number of photons (i.e., quantity of emr) being reflected off tissue from the part of the area of interest assigned to that pixel. For example, in a standard 512×512 image from a current technology CCD, there would be 262,144 pixels per image. In an 8 bit system, each pixel is represented by 8 bits. One can cool the CCD to reduce thermal noise.

Preferably, the signal processing means includes a programmable look-up table (e.g., CM150-LUT16, Imaging Technology, Woburn, Mass.) initialized with values for converting gray coded pixel values, representative of a black and white image, to color coded values based upon the intensity of each gray coded value. This provides image enhancement via an image stretch. An image stretch is a technique whereby the highest and lowest pixel intensity values used to represent each of the pixels in a digital image frame are determined over a region of the image frame which is to be stretched. Stretching a selected region over a larger range of values permits, for example, easier identification and removal of relatively high, spurious values due to noise (e.g., glare).

Each image received is stored in the frame buffer, preferably within the context of a CPU as a frame of data elements represented, for example, as a 512 by 512 array of pixels. Each pixel has a 8 bit value corresponding to one of 256 levels of gray.

The processing means further includes a plurality of frame buffers having frame storage areas for storing frames of digitized image data received from the A/D interface. The frame storage area comprises at least one megabyte of memory space, and preferably at least 8 megabytes of storage space. An additional 16-bit frame storage area is preferred as an accumulator for storing processed image frames having pixel intensities represented by more than 8-bits. The frame buffers are temporary fast memory. The processing means should include at least three frame buffers. One is for storing the averaged control image, another is for storing the subsequent image and a third is for storing a difference image between the averaged control image and the subsequent image.

The processing means further includes an arithmetic logic unit (ALU) (e.g., ALU-150 Pipeline Processor) for performing arithmetical (add, subtract, etc.) and logical (and, or, etc.) functions from data located in one or more frame buffers. An ALU is a fast processor. The ALU allows for image averaging in real time. For example, a newly incoming digitized image can be sent directly to the ALU and is added or subtracted to an averaged control image sitting in a frame buffer by passing both images through an ALU and adding them. After a last image is added, this 16 bit result can be sent again through an ALU which will divide this result by a constant (i.e., the total number of images). The output from the ALU is either stored in a frame buffer, sent for more processing, or used as its own input and again combined with another image.

The inventive apparatus can enhance processing speed to create a difference frame by adding a real time modular processor or faster CPU chip to the image processor. For example, one real time modular processor is a 150 RTMP-150 Real Time Modular Processor (Imaging Technology, Woburn, Mass.).

The processing means further may include a means for performing a histogram stretch of the difference frames (e.g., Histogram/Feature Extractor HF 151-1-V module, Imaging Technology, Woburn Mass.) to enhance each difference image across its dynamic range. A linear histogram stretch is described in, for example, Green, *Digital Image Processing: A Systems Approach*, Van Nostrand Reinhold, New York, 1983. A histogram stretch assigns the brightest pixel, or one with the highest value in the difference image and assigns this the maximum value. The smallest pixel value is assigned the minimum value and every other value in between is assigned a linear value (for a linear histogram stretch or a logarithmic value for a log histogram stretch, etc.) in between the maximum and minimum values. This allows the difference image to fully utilize the full dynamic range which provide for absolute changes.

The image processing system can use a variety of hardware. For example, the Texas Instrument Multimedia Video Processor (MVP) is for motion video applications. The MVP uses a highly parallel internal architecture, large on-chip memory, and extremely high bandwidth communication within CPU and between the CPU memory and I/O devices in order to provide in excess of 2 billion RISC-type operations per second performance necessary to support the requirement of real-time video compression standards and real-time image capture, processing and visualization. For example, the hardware can comprise of printed circuit board modules with interfaces to a VME bus. A single chassis can house all of the modules and reside on a rack that is easily transportable, along with display monitors and peripheral input and output devices. The real time system, for example, comprises four boards for acquisition image processing, peripheral control and host computer. A minimal configuration with reducing processing capabilities comprises just the acquisition and host computer boards. The acquisition board comprises circuitry to perform real-time averaging of incoming video frames and allow readout of averaged frames at a maximum rate bus. A VME bus is preferred because of its high peak bandwidth (greater than 80 Mbytes/sec for the latest revision, VME64) and compatibility with a multitude of existing VME products. The acquisition board must also support many different types of cameras via a variable scan interface. A daughter board can support the interfacing needs of many different types of cameras and supply variable scan signals to the acquisition motherboard. Preferably, the unit comprises a daughter board interfacing to an RS-170A video signal to support a wide base of cameras. Other camera types (such as slow scan cameras with a higher spatial/contrast resolution and/or better signal to noise ratio) can be developed and incorporated into the inventive device, as well as improved daughter boards to accommodate such improved cameras.

The host computer comprises a single-board embedded computer with a VME interface. Preferably the host computer comprises a VME64 interface, or a standard (IEEE 1014-1987) VME interface, depending upon bus bandwidth considerations. Example of host computer boards include, for example, Force SPARC/CPU-2E and HP9000 Model 7471. The user interface can be, for example, a Unix/X-Widow environment. The image processing board can be, for example, based upon Texas Instruments' MVP and other chips to perform real time image averaging, registration and other processing necessary to produce high quality difference images for intraoperative viewing. This board will also drive a 120×1024 RGB display to show a sequence of difference images over time with pseudo-color mapping to highlight tumor tissue. Preferably, a second monitor is used for the host computer to increase the overall screen real estate and smooth the user interface. The processing board (fully programmable) can support a VME64 master interface to control data transactions with the other boards. Lastly, a peripheral control board can provide electrical interfaces to control mechanical interfaces from the host computer. Such mechanical interfaces can include, for example, a computer-controlled, motor-driven syringe for dye injection, light source, and camera control box.

The difference image signal is, preferably, further processed to smooth out the image and remove high frequency noise. For example, a lowpass spatial filter can block high spatial frequencies and/or low spatial frequencies to remove high frequency noises at either end of the dynamic range. This provides a smoothed-out processed difference image (in digital format). The digitally processed difference image can be color-coded by assigning a spectrum of colors to differing shades of gray. This image is then converted back to an analog image (by an ADI board) and displayed for a real time visualization of differences between an averaged control image and subsequent images. Moreover, the processed difference image can be superimposed over the analog image to display regions upon a video display of the area of interest, those specific tissue sites where the dye may have a faster uptake or where an intrinsic signal may be occurring.

The present invention further includes a means for subtractive processing of difference images to identify cortical areas of neuronal inhibition. Normally areas of increased neuronal activity result in an increase of the emr absorption capacity of neuronal tissue (i.e., the tissue gets darker if visible light is used for emr illumination, or an intrinsic signal increases in a positive direction). Similarly, a decrease in neuronal activity results in a decrease of emr absorption capacity of the tissue (i.e., the tissue appears brighter, or intrinsic signals become negative). For example, image A is a subsequent averaged image and image B is an averaged control image. Normally, when a pixel in image A is subtracted from a pixel in image B and a negative value results, this value is treated as zero. Hence, difference images cannot account for areas of inhibition. However, the present invention provides a method for identifying both negative and positive intrinsic signals, by the method comprising: (a) subtracting image A (a subsequent averaged image) from image B (an averaged control image) to create a first difference image, whereby all negative pixel values are zero; and (b) subtracting image B from image A to create a second difference image whereby all negative pixel values are zero; and adding the first and second difference images to create a "sum difference image". The sum difference image shows areas of increased activity (i.e., color coded with warmer colors such as yellow, orange, red) and show areas of less activity or inhibition (i.e., color coded with colder colors such as green, blue, purple). Alternatively, one can overlay the first difference image on the second difference image.

Preferably, the processing means further includes an optical disk for storing digital image data, a printer for providing a hard copy of the digital and/or analog video image and a monitor to continuously monitor the difference frame output (converted back to an analog signal) of the apparatus. The difference frame output may be superimposed upon the real time analog video image to provide a video image of the area of interest superimposed with a color-coded difference frame, in frozen time.

EXAMPLE 1

This example provides a series of studies using hippocampal slices to investigate the effects of furosemide on epileptiform discharges. During these studies, spontaneous epileptiform activity was elicited by a variety of treatments. Sprague-Dawley rats (males and females; 25–35 days old) were decapitated, the top of the skull was rapidly removed, and the brain chilled with ice-cold oxygenated slicing medium. The slicing medium was a sucrose-based artificial cerebrospinal fluid (sACSF) consisting of (in mM) 220 mM sucrose, 3 mM KCl, 1.25 mM $NaH_2PO_4$, 2 mM $MgSO_4$, 26 mM $NaHCO_3$, 2 mM $CaCl_2$, and 10 mM dextrose (295–305 mOsm; measured with an osmomoter). A hemisphere of brain containing hippocampus was blocked and glued (cyanoacrylic adhesive) to the stage of a Vibroslicer (Frederick Haer, Brunswick, Me.). Horizontal or transverse slices 400 $\mu$m thick were cut in 4° C., oxygenated (95% $O_2$; 5% $CO_2$) slicing medium. The slices were immediately transferred to a holding chamber where they remained submerged in oxygenated bathing medium (ACSF) consisting of 124 mM NaCl, 3 mM KCl, 1.25 mM $NaH_2PO_4$, 2 mM $MgSO_4$, 26 mM $NaHCO_3$, 2 mM $CaCl_2$, and 10 mM dextrose (295–305 mOsm). The slices were held at room temperature for at least 45 minutes before being transferred to a submersion-style recording chamber (stimulation-evoked after discharge experiments) or an interface recording chamber (all other experiments). In the recording chamber, the slices were perfused with oxygenated recording medium at 34–35° C. All animal procedures were in accordance with NIH and University of Washington animal care guidelines. In most slice experiments, simultaneous extracellular field electrode recordings were obtained from CA1 and CA3 areas. A bipolar tungsten stimulating electrode was placed on the Schaffer collaterals so as to evoke synaptically-driven field responses in CA1. Stimuli consisted of 100–300 $\mu$sec duration pulses at an intensity of four times population-spike threshold. After discharges were evoked by a 2 second train of such stimuli delivered at 60 Hz. Spontaneous interictal-like bursts were observed in slices treated by the following modifications or additions to the bathing medium: 10 mM potassium (6 slices; 4 animals; average—81 bursts/min.); 200–300 $\mu$M 4-aminopyridine (4 slices; 2 animals; average—33 bursts/min.); 50–100 $\mu$M bicuculline (4 slices; 3 animals; average—14 bursts/min); 0 mM $Mg^{++}$ (1 hour of perfusion—3 slices; 2 animals; average—20 bursts/min or 3 hours of perfusion—2 slices; 2 animals); zero calcium/6 mM KCl and 2 mM EGTA (4 slices; 3 animals). In all treatments, furosemide was added to the recording medium once a consistent level of bursting was established.

In the first of these procedures, episodes of after discharges were evoked by electrical stimulation of the Schaffer collaterals (Stasheff et al., Brain Res. 344:296, 1985) and the extracellular field response was monitored in the CA1 pyramidal cell region (13 slices; 8 animals). The concentration of $Mg^{++}$ in the bathing medium was reduced to 0.9 mM and after discharges were evoked by stimulation at 60 Hz for 2 seconds at an intensity 4 times the population spike threshold (population spike threshold intensity varied between 20–150 $\mu$A at 100–300 $\mu$sec pulse duration). The tissue was allowed to recover for 10 minutes between stimulation trials. In each experiment, the initial response of CA1 to synaptic input was first tested by recording the field potential evoked by a single stimulus pulse. In the control condition, Schaffer collateral stimulation evoked a single population spike (FIG. 1A, inset). Tetanic stimulation evoked approximately 30 seconds of after discharge (FIG. 1A, left) associated with a large change in intrinsic signal (FIG. 1A, right).

For imaging of intrinsic optical signals, the tissue was placed in a perfusion chamber located on the stage of an upright microscope and illuminated with a beam of white light (tungsten filament light and lens system—Dedo Inc.) directed through the microscope condenser. The light was controlled and regulated (power supply—Lamda Inc.) to minimize fluctuations and filtered (695 nm longpass) so that the slice was transilluminated with long wavelengths (red). Field of view and magnification were determined by the choice of microscope objectives (4× for monitoring the entire slice). Image-frames were acquired with a charge-coupled device (CCD) camera (Dage MTI Inc.) at 30 Hz and were digitized at 8 bits with a spatial resolution of 512×480 pixels using an Imaging Technology Inc. Series 151 imaging system; gains and offsets of the camera-control box and the A/D board were adjusted to optimize the sensitivity of the system. Imaging hardware was controlled by a 486-PC compatible computer. To increase signal/noise, an averaged-image was composed from 16 individual image-frames, integrated over 0.5 sec and averaged together. An experimental series typically involved the continuous acquisition of a series of averaged-images over a several minute time period; at least 10 of these averaged-images were acquired as control-images prior to stimulation. Pseudocoloured images were calculated by subtracting the first control-image from subsequently acquired images and assigning a color lookup table to the pixel values. For these images, usually a linear low-pass filter was used to remove high frequency noise and a linear-histogram stretch was used to map the pixel values over the dynamic range of the system. All operations on these images were linear so that quantitative information was preserved. Noise was defined as the maximum standard deviation of fluctuations of ΔR/R the sequence of control images within a given acquisition series, where ΔR/R represented the magnitude of the change in light-transmission through the tissue. Delta R/R was calculated by taking all the difference-images and dividing by the first control image: (subsequent image—first-control-image)/first-control-image. The noise was always<0.01 for each of the chosen image sequences. The absolute change in light transmission through the tissue was estimated during some experiments by acquiring images after placing neutral density filters is between the camera and the light source. On average, the camera electronics and imaging system electronics amplified the signal 10-fold prior to digitization so that the peak absolute changes in light transmission through the tissue were usually between 1% and 2%.

Epileptiform after discharges or spontaneous bursts were evoked in hippocampal slices by electrical stimulation or by perfusion with medium containing either bicuculline, 4-AP, high-$K^+$, low-Mg+, or zero-$Ca_2$+. Furosemide, a chloride cotransport inhibitor, reversibly blocked the epileptiform discharges elicited by each of these treatments even though the field response to single-pulse synaptic drive was either unaffected or enhanced. Images acquired during these slice experiments indicated that furosemide blocked changes in the intrinsic optical signal, associated with cell swelling, coincident with its inhibition of spontaneous epileptiform activity. In urethane-anesthetized rats, field recordings from the cortex showed that systemically-injected furosemide blocked kainic acid-induced electrical discharges.

After 10 minutes of perfusion with 2.5 mM furosemide added to the bathing medium, after discharge activity and associated optical changes were completely blocked (FIG. 1B). However, at the same time, multiple population spikes were elicited by the single test pulse (FIG. 1B, inset). These opposing effects of furosemide-blockade of the stimulation-evoked after discharges and a concomitant increase of the synaptic response to a test-pulse—illustrate the two key results that were observed in all in vitro models: (1) furosemide blocked epileptiform activity, and (2) synchronization (as reflected in spontaneous epileptiform activity) and excitability (as reflected in the response to a single synaptic input) were dissociated. Experiments in which the dose-dependency of furosemide was examined determined that a minimum concentration of 1.25 mM was required to block both the after discharges and optical changes.

EXAMPLE 2

Figure 1D:
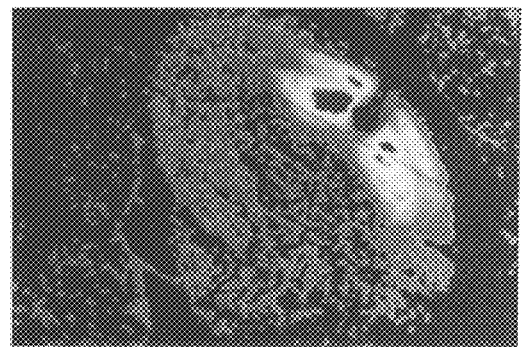
Figure 1D:
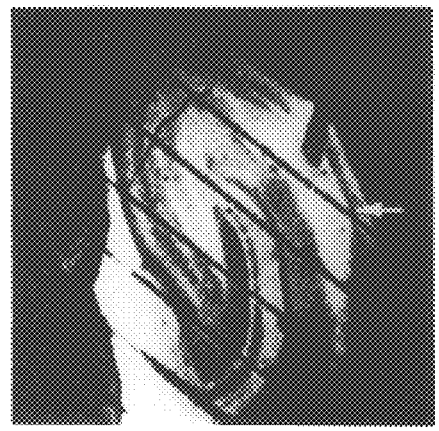
Figure 2A:
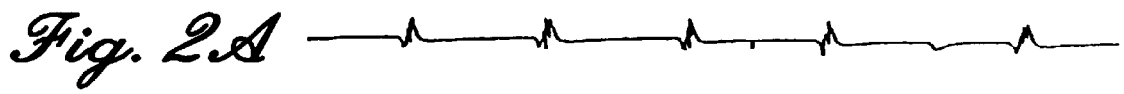
FIG. 2A demonstrates that epileptiform activity was induced by slice perfusion with bathing medium containing 10 mM potassium. Field recordings were obtained simultaneously from CA3 (top trace) and CA1 (bottom trace) pyramidal cell layers. (1): Regular bursting was elicited prior to the addition of furosemide to the recording medium. (2): After 15 minutes of perfusion with furosemide (2.5 mM), the bursts occurred with increased magnitude, possibly reflecting the effects of furosemide on inhibition. (3): After 45 minutes of furosemide perfusion, spontaneous bursts were blocked. (4): Recovery of the high-induced bursting pattern was seen within one hour of return to perfusion with normal bathing medium.

This example illustrates a second series of slice experiments, wherein spontaneous synchronized bursting activity was generated in slices perfused with high-K+ (10 mM) bathing medium (Traynelis et al., *J. Neurophysiol.* 59:259, 1988). Slices were perfused with a high-$K^+$ solution until extended periods of spontaneous interictal-like bursting were recorded simultaneously in CA1 and CA3 pyramidal cell regions (FIG. 2A1). After 15 minutes of perfusion with furosemide-containing medium (2.5 mM furosemide), the burst discharges increased in magnitude (FIG. 2A2). However, after 45 minutes of furosemide perfusion, the bursts were blocked in a reversible manner (FIG. 2A3, 2A4). During this entire sequence of furosemide perfusion, the synaptic response to a single test pulse delivered to the Schaffer collaterals was either unchanged or enhanced during the furosemide block (data not shown). It is possible that the initial increase in discharge amplitude reflected a furosemide-induced decrease in inhibition (Misgeld et al, Science 232:1413 1986; Thompson et al., *J. Neurophysiol.* 60:105, 1988; Thompson and Gähwiler, *J. Neuropysiol.* 61:512, 1989; and Pearce, *Neuron* 10:189, 1993). It has previously been reported (Pearce, *Neuron* 10:189, 1993) that furosemide blocks a component of the inhibitory currents in hippocampal slices with a latency (<15 min.) similar to the time to onset of the increased excitability observed here. The longer latency required for the furosemide-block of the spontaneous bursting might correspond to additional time required for a sufficient block of the furosemide-sensitive cellular volume regulation mechanisms under high-$K^+$ conditions.

Figure 2B:
FIG. 2B illustrates prolonged periods of regular that were recorded from the entorhinal cortex (1) and the subiculum (data not shown) following 3 hours of perfusion with bathing medium containing no magnesium. This discharge pattern, similar to activity previous shown to be resistant to conventional anticonvulsants blocked (2) after 60 minutes of perfusion with medium containing 2.5 mM furosemide.
Figure 2C:
FIG. 2C shows in bathing medium containing 200 $\mu$M 4-aminopyridine, spontaneous synchronous bursts were recorded in CA3 (1) and in CA1 (data not shown). After 30 minutes of exposure to 2.5 mM furosemide, this activity was blocked (2).
Figure 2D:
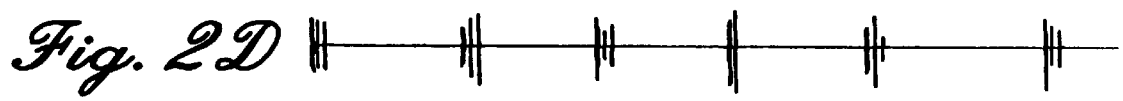
FIG. 2D shows that bicuculline (100 $\mu$M; CA3 recording shown)
Figure 2E:
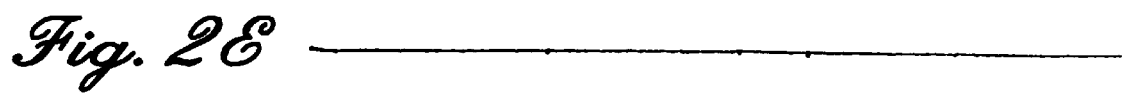
FIG. 2E shows that zero-magnesium (1 hour; CA1 recording shown) treatments also gave rise to interictal-like discharges that were blocked by furosemide (2.5 mM).
Figure 2F:
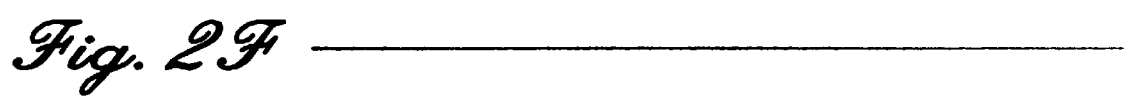
FIG. 2F shows that tissue treated with bathing medium containing no calcium (and added EGTA) showed slow, rhythmic membrane shifts in CA1 (1). These non-synaptically-mediated epileptiform events were also completely blocked (2) after perfusion with furosemide (5 mM).
Figure 2G:
FIG. 2 shows furosemide blockade of spontaneous epileptiform burst discharges across a variety of in vitro models.
Figure 2H:
Figure 2I:
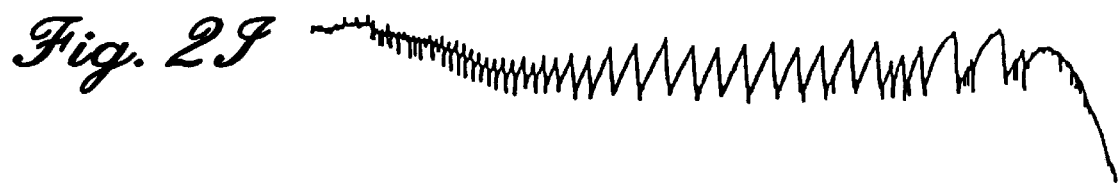
Figure 2J:
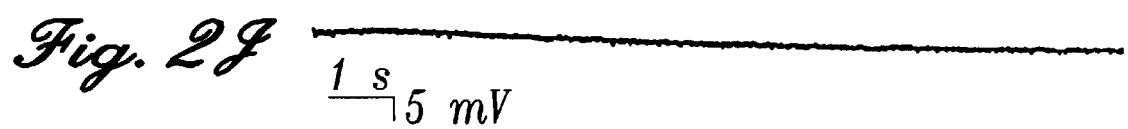
Figure 2K:
Figure 2L:
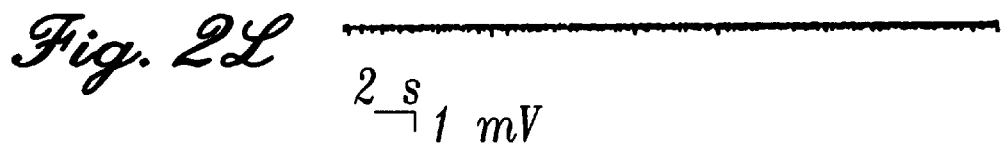
Figure 2M:
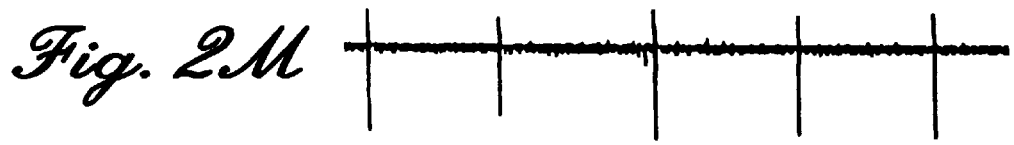
Figure 2N:
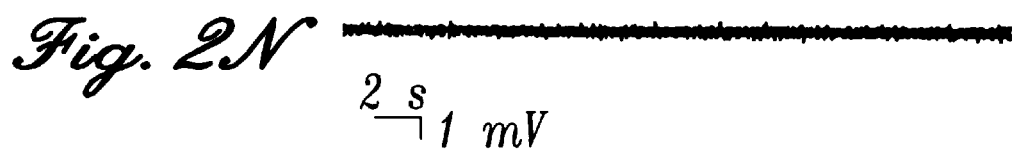
Figure 2O:
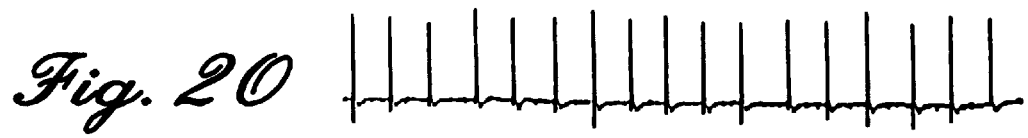
Figure 2P:
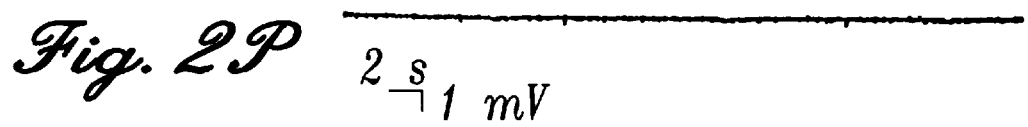
Figure 2Q:
Figure 2R:
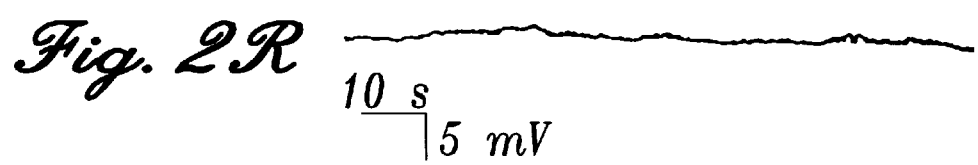

After testing the effects of furosemide on slices perfused with high-$K^+$, similar studies were performed with a variety of other commonly studied in vitro models of epileptiform discharge (Galvan et al., *Brain Res.* 241:75, 1982; Schwartz-kroin and Prince, *Brain Res.* 183:61, 1980; Anderson et al., *Brain Res.* 398:215, 1986; and Zhang et al., *Epilepsy Res.* 20:105, 1995). After prolonged exposure to 0-$Mg^{++}$ (2–3 hours), slices have been shown to develop epileptiform discharges that are resistant to common clinically used anticonvulsant drugs (Zhang et al., *Epilepsy Res.* 20:105, 1995). Our recordings from entorhinal cortex (FIG. 2B1) and subiculum (not shown) showed that after 3 hours of perfusion with 0-$Mg^{++}$, slices developed bursting patterns that appeared similar to these previously described "anticonvulsant resistant" bursts. One hour after the addition of furosemide to the bathing medium, these bursts were blocked (FIG. 2B2). Furosemide also blocked spontaneous burst discharges observed with the following additions/modifications to the bathing medium: 1) addition of 200–300 μM 4-aminopyridine (4-AP; a potassium channel blocker) (FIG. 2C); 2) addition of the GABA antagonist, bicuculline, at 50–100 μM (FIG. 2D); 3) removal of magnesium (0-Mg++)—1 hour perfusion (FIG. 2E); and, 4) removal of calcium plus extracellular calcium chelation (0-$Ca^{++}$) (FIG. 2F). With each of these manipulations, spontaneous interictal-like patterns were simultaneously recorded from the CA1 and CA3 subfields FIGS. 2C and 2D show only the CA3 trace and FIGS. 2E and 2F show only CA1 trace). In the 0-$Ca^{++}$ experiments, 5 mM furosemide blocked the bursting with a latency of 15–20 minutes. For all other protocols, bursting was blocked by 2.5 mM furosemide with a latency of 20–60 minutes. Furosemide reversibly blocked the spontaneous bursting activity in both CA1 and CA3 in all experiments (FIG. 2C2, 2D2, 2E2, 2F2).

EXAMPLE 3

This example illustrates an in vivo model in which epileptiform activity was induced by i.v. injection of kainic acid (KA) into anesthetized rats (Lothman et al., *Neurology* 31:806, 1981) (FIG. 3). Sprague-Dawley rats (4 animals; weights 250–270 g) were anesthetized with urethane (1.25 g/kg i.p.) and anesthesia maintained by additional urethane injections (0.25 g/kg i.p.) as needed. Body temperature was monitored using a rectal temperature probe and maintained at 35–37° C. with a heating pad; heart rate (EKG) was continuously monitored. The jugular vein was cannulated on one side for intravenous drug administration. Rats were placed in a Kopf stereotaxic device (with the top of the skull level), and a bipolar stainless-steel microelectrode insulated to 0.5 mm of the tip was inserted to a depth of 0.5–1.2 mm from the cortical surface to record electroencephalographic (EEG) activity in the fronto-parietal cortex. In some experiments a 2M NaCl-containing pipette was lowered to a depth of 2.5–3.0 mm to record hippocampal EEG. Data were stored on VHS videotape and analyzed off-line. Following the surgical preparation and electrode placement, animals were allowed to recover for 30 minutes before the experiments were initiated with an injection of kainic acid (10–12 mg/kg i.v.). Intense seizure activity, an increased heart rate, and rapid movements of the vibrissae were induced with a latency of about 30 minutes. Once stable electrical seizure activity was evident, furosemide was delivered in 20 mg/kg boluses every 30 minutes up to a total of 3 injections. Experiments were terminated with the intravenous administration of urethane. Animal care was in accordance with NIH guidelines and approved by the University of Washington Animal Care Committee.

In this model, intense electrical discharge (electrical "status epilepticus") was recorded from the cortex (or from depth hippocampal electrodes) 30–60 minutes after KA injection (10–12 mg/kg) (FIG. 3B). Control experiments (and previous reports, Lothman et al., Neurology 31:806, 1981) showed that this status-like activity was maintained for well over 3 hours. Subsequent intravenous injections of furosemide (cumulative dose: 40–60 mg/kg) blocked seizure activity with a latency of 30–45 minutes, often producing a relatively flat EEG (FIG. 3C, 3D). Even 90 minutes after the furosemide injection, cortical activity remained near normal baseline levels (i.e., that observed prior to the KA and furosemide injections). Studies on the pharmacokinetics of furosemide in the rat indicate that the dosages used in this example were well below toxic levels (Hammarlund and Paalzow, *Biophariiiaceutics Drug Disposition* 3:345, 1982).

Discussion of Examples 1–3

These experiments show that furosemide, a chloride cotransporter antagonist and common loop diuretic, blocked epileptiform activity in a wide variety of experimental models, even though a spectrum of different physiological mechanisms is thought to lead to the spontaneous discharges associated with each of the models tested. Furosemide likely acted on a common mechanism that is necessary for the generation of synchronized bursts. This common mechanism of action is likely to be nonsynaptic since furosemide did not block synaptic responses to electrical stimulation, but did block epileptiform discharge in zero calcium (where synaptic activity is absent). Further, although furosemide treatment blocked spontaneous epileptiform activity, it was also often associated with a "hyperexcited" synaptic response likely due to its effect on chloridemediated neuronal inhibition (Misgeld et al, *Science* 232:1413, 1986; Thompson et al., *J. Neurophysiol.* 60:105, 1988; Thompson and Gähwiler, *J. Neuropysiol.* 61:512, 1989; and Pearce, *Neuron* 10:189, 1993). Thus, furosemide dissociates a pure increase in synaptic excitability from hypersynchronization that characterizes all forms of seizure activity.

The nonsynaptic mechanisms that underlie furosemide's action are related to cell-volume regulation, and in particular to glial swelling. This hypothesis is supported by the observation that stimulation-evoked changes in optical transmission, through the slice tissue, were blocked coincidentally with furosemide block of spontaneous discharges. This mechanism of action is also be consistent with previous findings that alterations in osmolarity can block spontaneous bursts in some models of epilepsy (Traynelis et al., *J. Neurophysiol.* 59:259, 1988; Dudek et al., *Neurosci. Letters* 120:267, 1990; Baran et al., *Neuroscience* 21:679, 1987; Carter, *Epilepsia* 3:198, 1962; and Read and Woodbury, *J. Pharmacol.* 146:154, 1964). Similar mechanisms play a role in normal cortical function, particularly that associated with rhythmic synchronized oscillatory behaviors (Osehobo and Andrew, *Exp. Neurol.* 124:192, 1993). Finally, epileptiform activity and normal cortical activity involved in sensory, motor, and language tasks are associated with optical changes in the awake human cortex (Haglund et al., *Nature* 358:668, 1992).

One early diagnostic procedure for epilepsy involved the oral administration of large quantities of water together with injections of vasopressin to prevent the accompanying diuresis. This treatment was found to induce seizures in epileptic patients, but rarely in non-epileptic individuals (Garland et al., *Lancet* 2:566, 1943). At the level of experimental treatments, status epilepticus can be blocked in kainic acid-treated rats by intravenous injection of mannitol (Baran et al., *Neuroscience* 21:679, 1987). This effect is similar to that achieved by intravenous injection of urea in human patients (Carter, *Epilepsia* 3:198, 1962). The treatment in each of these cases increases the osmolarity of the blood and extracellular fluid, resulting in water efflux from the cells and an increase in ECS. Given that furosemide is safely used as a loop diuretic, these data suggest that it or other related compounds will find clinical utility as antiepileptic agents. Acetazolamide (ACZ), another diuretic with a different mechanism of action (inhibition of carbonic anhydrase), has been studied experimentally as an anticonvulsant (White et al., *Advance. Neurol.* 44:695, 1986; and Guillaume et al, *Epilepsia* 32:10, 1991) and used clinically on a limited basis (Tanimukai et al., *Biochem. Pharm.* 14:961 1965; and Forsythe et al., *Develop. Med. Child Neurol.* 23:761 1981). Although its mechanisms of anticonvulsant action has not been determined, ACZ does have a clear effect on ECS, which is consistent with the proposed mechanism of action of furosemide. Modulation of the ECS plays a critical role in neuronal synchronization.

I claim:

1. a method for screening drug candidate compounds for anti-epileptic activity comprising:
   (a) providing a culture of viable glial cells and dividing the culture into components that will become control samples and test samples;
   (b) adding a glial cell stressing agent at a concentration that is capable of osmotically shocking the glial cells but not killing the glial cells;
   (c) adding the drug candidate at varying concentrations to only test samples of glial cells; and
   (d) measuring whether the drug candidate in the test samples is capable of abating changes in glial cell swelling in the control samples when measured by a means for measuring cellular dimensions over time.

2. The method of claim 1 wherein the measuring means for glial cell swelling measures intrinsic optical signals.

3. The method of claim 2 wherein the means for measuring intrinsic optical signals is by comparing digitized video images of the cell culture magnified and then subtracting the digitized images after addition of the stressing agent to form a changes images that can integrate cellular swelling changes measure over time.

4. The method of claim 1 wherein the glial cell stressing agent is a hypotonic medium having lowered $Mg^{++}$ concentrations.

5. A a method for screening drug candidate compounds for activity to prevent or treat symptoms of Alzheimer's disease comprising:
   (a) providing a culture of viable CNS-based cells and dividing the culture into components that will become control samples and test samples;

(b) adding a sensitization agent at a concentration that is capable of inducing apoptosis in the glial cells but not killing the glial cells and further adding an osmotic stressing agent;

(c) adding the drug candidate at varying concentrations to only test samples of CNSbased cells; and (d) measuring whether the drug candidate in the test samples is capable of abating changes in cell swelling in the control samples when measured by a means for measuring cellular dimensions over time.

6. The method of claim 5 wherein the CNS-based cells are selected from the group consisting of glial cells, neuronal cells, microglia, astrocytes, and combination cultures thereof.

7. The method of claim 5 wherein the sensitization agent is selected from the group consisting of BAP and derivatives thereof, glutamate, IFN-γ (interferon gamma), TNFα (tumor necrosis factor alpha), and combinations thereof.

8. The method of claim 5 wherein the measuring means for glial cell swelling measures intrinsic optical signals.

9. The method of claim 8 wherein the means for measuring intrinsic optical signals is by comparing digitized video images of the cell culture magnified and then subtracting the digitized images after addition of the stressing agent to form a changes images that can integrate cellular swelling changes measure over time.

10. The method of claim 5 wherein the osmotic stressing agent is a hypotonic medium having a lowered $Mg^{++}$ concentration.

11. A method for determining cell viability and health of living cells inside polymeric tissue implants, comprising:

(a) providing a sample of tissue implants comprising living cells inside a polymeric matrix;

(b) measuring the cellular dimensions of the living cells inside the tissue implant by determining cellular dimensions with a microscopic means for determining digitized video images over time.

(c) adding a hypo osmotic stressing agent at a concentration that is capable of osmotically shocking the living cells but not killing the living cells; and (d) measuring whether the osmotic stressing agent was capable of inducing changes in living cell swelling which would indicate poor health of the living cells.

12. The method of claim 11 wherein the measuring means for living cell swelling measures intrinsic optical signals.

13. The method of claim 12 wherein the means for measuring intrinsic optical signals is by comparing digitized video images of the living cells culture magnified and then subtracting the digitized images after addition of the stressing agent to form a changes images that can integrate cellular swelling changes measure over time.

14. The method of claim 11 wherein the cell stressing agent is a hypotonic medium having a lowered $Mg^{++}$ concentration.

* * * * *